United States Patent [19]
Fujii et al.

[11] Patent Number: 5,789,579
[45] Date of Patent: Aug. 4, 1998

[54] ACIDIC POLYSACCHARIDE

[75] Inventors: Noboru Fujii, Miyazaki; Genichi Kadota, Kumamoto-ken, both of Japan

[73] Assignees: Kabushikigaisha Sophy, Kochi-ken, Japan; Frederick L. Luth; James J. King, both of Garland, Tex.; Leo C. Johnson, Dallas, Tex.

[21] Appl. No.: 785,901

[22] Filed: Jan. 21, 1997

Related U.S. Application Data

[62] Division of Ser. No. 406,584, Mar. 20, 1995, Pat. No. 5,646,270.

[30] Foreign Application Priority Data

Mar. 22, 1994 [JP] Japan .................. 6-73784

[51] Int. Cl.$^6$ .............. C07H 13/02; C07H 1/00; C12P 19/00; C12P 19/04
[52] U.S. Cl. .............. 536/119; 536/115; 536/124; 435/72; 435/101; 435/102
[58] Field of Search .................. 536/119, 115, 536/124; 435/72, 101, 102

[56] References Cited

U.S. PATENT DOCUMENTS

| | | | |
|---|---|---|---|
| 4,230,800 | 10/1980 | Takayama et al. | 435/101 |
| 4,276,379 | 6/1981 | Heady | 435/94 |
| 4,280,954 | 7/1981 | Yannas et al. | 260/123.7 |
| 4,330,533 | 5/1982 | Takayama et al. | 435/101 |
| 4,420,397 | 12/1983 | Kaneko et al. | 435/254 |
| 4,423,150 | 12/1983 | Heady | 435/193 |

OTHER PUBLICATIONS

Hamada et al, Agric. Biol. Chem., 47(6), 1167–1172, 1983.

*Primary Examiner*—John Kight
*Assistant Examiner*—Everett White
*Attorney, Agent, or Firm*—Oblon, Spivak, McClelland, Maier & Neustadt, P.C.

[57] ABSTRACT

The invention provides an acidic polysaccharide by culturing acidic polysaccharide-producing germ belonging to *Aureobasidium sp.* isolated from soil, which has no toxicity and is applicable to growth promotion by adding to feed, waste water-treating agent and foods.

12 Claims, 8 Drawing Sheets

ACIDIC POLYSACCHARIDE

This application is a division of Ser. No. 08/406,584, filed Mar. 20, 1995, now U.S. Pat. No. 5,646,270.

BACKGROUND OF THE INVENTION

The present invention relates to a process for producing a novel acidic polysaccharide from *Aureobasidium sp.* isolated from soil and a food additive, feed additive, waste water-treating agent, etc. containing this acidic polysaccharide.

A process for producing agglutination-active substance obtainable by an agglutination-active substance-producing bacteria belonging to, for example, *Dematium sp.* bacteria, a method for agglutinating treatment of waste water using this substance, etc. disclosed in Japanese Patent Publication No. Sho 58-47159, Japanese Patent Publication No. Sho 59-7518, etc. The present invention provides a process for producing the novel acidic polysaccharide from a microorganism different from those above and, a food additive, feed additive, waste water-treating agent, etc. contains this acidic polysaccharide.

The microorganism used in the present invention is a bacteria of Fermentation Research Institute Deposit No. P-14228 (FERM P-14228). The bacteria of the invention is one belonging to *Aureobasidium sp.* isolated from soil, which produces the novel polysaccharide of the present invention.

SUMMARY OF THE INVENTION

The present invention provides an acidic polysaccharide by culturing acidic polysaccharide-producing bacteria belonging to *Aureobasidium sp.* isolated from soil, which has no toxicity and is useful for growth promotion by adding to feed, waste water-treating agent and foods.

DETAILED DESCRIPTION OF THE INVENTION

Figure 1:
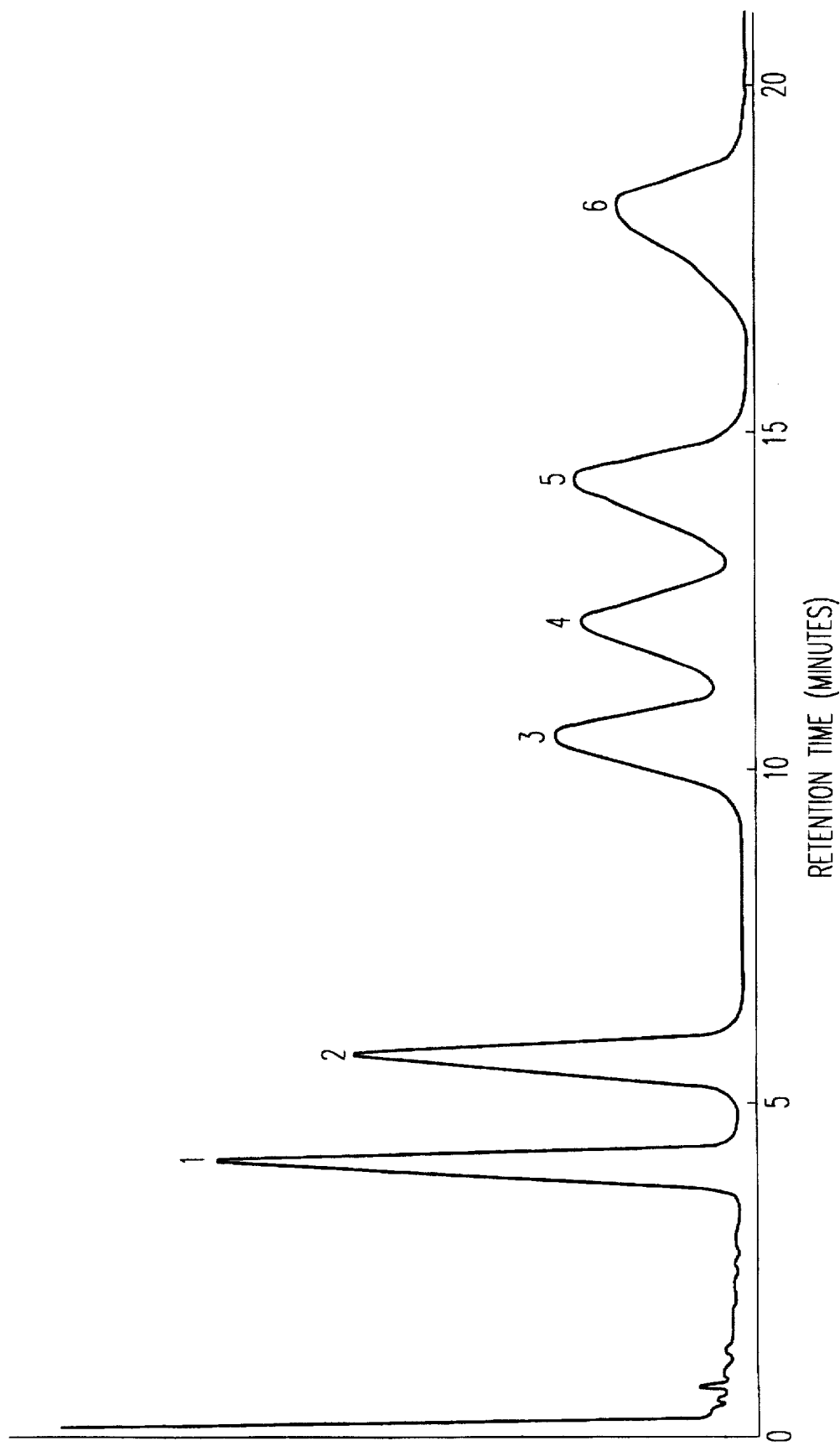
FIG. 1 shows a chromatogram of an alditol acetate standard.

In following, the mycological features will be explained.

Mycological features of the bacteria producing the inventive polysaccharide

With the bacteria isolated from soil, when culturing for 24 hours at 25° C. on a slant medium of potato-dextrose agar (from Nippon Suisan Kaisha, Ltd.), the colonies have smooth surface and pale grayish white color, they become light black after 48 hours, the periphery of each colony shows filiform growth and changes gradually to yeast-like growth, and the surface of colonies becomes light dark black after 72 hours and then overall the surface turns a light dark black color. On plate culture, the colonies show filiform growth radially, which become black gradually.

In a liquid medium of potato-dextrose, black colonies grow on the liquid surface and, on shaking, the culture liquid appears viscous. Precipitation of bacteria can be seen at the bottom of tube.

According to microscopic observation, the cells are in the form of filaments and viscous substances are formed at the periphery of germs after culturing for 24 hours. The width of cell is 1.0 to 2.5 μm and septums are observed in places of bacterial growth. With lapse of time, these septums are broken to become segmental cells. Moreover, from the side walls of filiform cells, yeast-like budding segments are formed. The shape thereof is oval and the size is 4–7×3–4 μm. Often, thereamong, large oval-spherical spore-like cells with brown thick wall are also formed. In addition, long chain-like cells are also seen.

The growing temperature of 20° to an optimum temperature is 25° C., and growable temperature and is 5° to 40° C., and optimum pH value of 5 to 6. The germ decomposes hexoses such as glucose, fructose and galactose, disaccharides such as sucrose, and starch, and, with all carbon sources, the culture liquid becomes viscous, and has a peculiar aroma.

Based on the mycological features as describe above, we Aureobasidium strain of *Aureobasidium sp.*

EXAMPLE

Production of polysaccharide with the bacteria

Culturing of the bacteria as it is results in black color, but, if cultured on a medium containing vitamin E and Lecithin as an emulsifier at the time of culture, then it results in light black grayish white color compared with the case of no addition, thus inhibiting blackening, to give a remarkably viscous culture liquid. Namely, the medium composition for culturing the germ is 1% cane sugar, 0.2% rice bran, 0.2% lecithin, 0.2% vitamin E and 100 ml of water, pH value being 5.2. After sterilizing this culture liquid with a high-pressure steam of 1 kg/cm$^2$, the bacteria is inoculated, and, after cultured under aeration and stirring in a jar fermenter for 12 hours at 25° C., 0.5 ml/min and 100 rpm, the content is sterilized for 15 minutes with high-pressure steam of 1 kg/cm$^2$ to obtain a supernatant (polysaccharide) by centrifugal separation for 15 minutes at 10000 rpm.

This supernatant after culturing has a remarkable viscosity. When this polysaccharide-containing culture liquid is stirred while adding two-fold volume of ethanol, the agglutination of the polysaccharide occurs. By collecting the polysaccharide and freeze-drying it, the polysaccharide in a yield of 55% based on sugar can be obtained. The medium shown in Table 1.

TABLE 1

Composition of medium for producing polysaccharide

| Component | Amount |
| --- | --- |
| Rice bran | 0.2 g |
| Sugar | 1.0 g |
| Lecithin (nacalai tesque) | 0.2 g |
| Vitamin E (nacalai tespue) | 0.2 g |
| Distilled water | 100 ml |
| pH | 5.2 |

Purification of polysaccharide for analytical sample

After the culture liquid treated for 72 hours in a jar fermenter was centrifugally separated for 15 minutes at 8000 rpm, the supernatant was treated by the Sevag method to remove lipid, protein, etc. Namely, a mixed solution of chloroform:butanol=5:1 was added in amount of 10% to culture liquid, which was stirred for 24 hours. Then, this solution was subject to centrifugal separation for 15 minutes at 12000 rpm to remove the germ and the supernatant was collected. This procedure was repeated thrice.

Next, after adding two-fold volume of ethanol to this culture liquid, the polysaccharide agglutinates to precipitate. This agglutinant (polysaccharide) was filtered off to remove ethanol and dissolved into distilled water under cooling with water and stirring. This was agglutinated again by adding three-fold volume of ethanol and allowed to stand for 1 hour at 70° C. to remove coloring matter. Then, this agglutinant was subject to centrifugal separation for 15 minutes at 10000 rpm. This procedure was repeated. This agglutinant was dissolved again into water and cetavlon was added in proportion of 3 mg to 1 mg of agglutinant to form precipitate. This substance was washed with distilled water and dissolved again into 1NMgSO$_4$. To this solution, three-fold volume of ethanol was added to obtain precipitates, which were washed enough with ethanol. The precipitates were dissolved into distilled water, and, after dialyzed for 2 days in running water through a cellulose dialysis membrane, the solution was dialyzed further for 1 day in distilled water. Then, the dialyzed inner solution was freeze-dried to obtain purified polysaccharide. The yield of polysaccharide was 3.5 mg/ml.

Physical and chemical properties of the substance

1) Relative viscosity

Relative viscosity of 0.1% solution of purified polysaccharide was measured with Ostwald viscosimeter. As references for comparison, 0.1% solutions of dextran and starch were employed. The measurement results are shown in Table 2, in which the inventive polysaccharide has a viscosity three times or more as high as those of the comparative polysaccharides.

TABLE 2

| Polysaccharides (0.1% solution) | Relative viscosity (cp) |
| --- | --- |
| Starch | 0.833 |
| Dextran | 0.847 |
| Present polysaccharide | 2.721 |

2) Identification of constitutional monosaccharides

The purified polysaccharide was converted to alditol acetate by the alditol acetate conversion method. That is, the polysaccharide was hydrolyzed to afford monosaccharides and reduced with sodium borohydride to the convert to corresponding alditol acetates. These were acetylated with acetic anhydride and pyridine to convert to alditol acetate derivatives. The alditol acetate derivatives were recored on gas chromatogram to estimate the relative retention time of each peak, using inositol as a standard.

By comparing the relative retention time of each monosaccharide of standard sample with that of sample, the identification of constitutional sugars was performed. Namely, a Shimazu Gas Chromatography GC-8APF was used and, for the column, a glass column tube (3.2 mmφ×2 m) packed with ECNSS-M was employed. It was used at a constant column temperature of 190° C., injection port temperature of 300° C. and pressure of 2.0 kgf/cm$^2$, nitrogen as the carrier gas.

Figure 2:
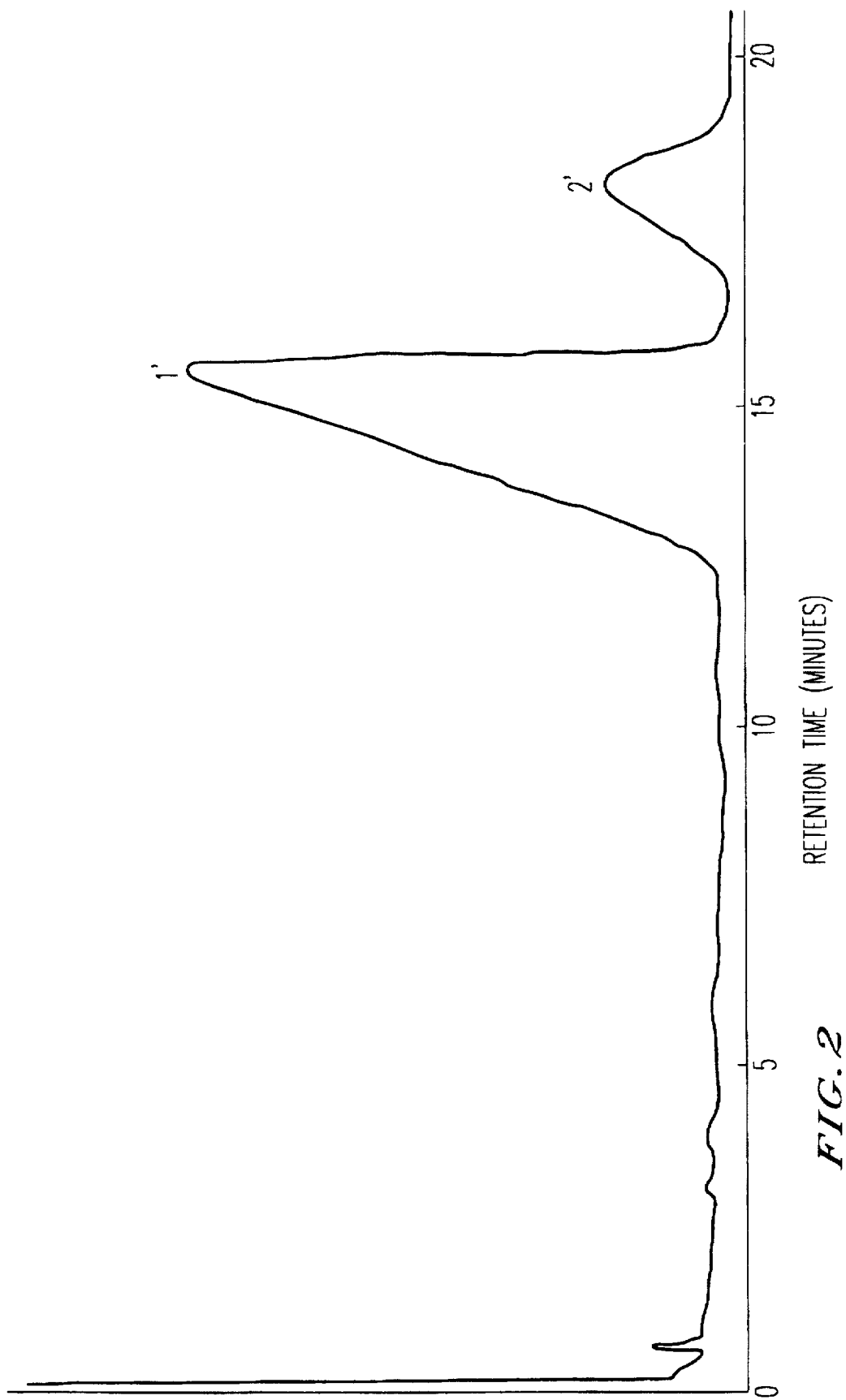
FIG. 2 shows a chromatogram, of alditol acetate of the inventive polysaccharide.

From the as chromatograms shown in FIG. 1 and FIG. 2, a peak 1' in FIG. 2 was assumed to be glucose, comparing with FIG. 1.

Next, from the results of Tables 3 and 4, the content of monosaccharide was determined and found to be 95.5%, thus the polysaccharide is a homoglucan composed of only glucose.

TABLE 3

Results of gas chromatography of standard alditol acetate

| Peak | material | Retention time (min) | Standard concentration (mg/ml) | Relative retention time | Area (g) |
| --- | --- | --- | --- | --- | --- |
| 1 | Arabinose | 4.05 | 1.004 | 0.2213 | 0.0418 |
| 2 | Xylose | 5.70 | 1.003 | 0.3115 | 0.0395 |
| 3 | Mannose | 10.50 | 1.006 | 0.5734 | 0.0333 |
| 4 | Galactose | 12.15 | 1.007 | 0.6639 | 0.0266 |
| 5 | Glucose | 14.25 | 1.000 | 0.7787 | 0.0362 |
| 6 | Inositol | 18.30 | 1.007 | 1.0000 | 0.0363 |

TABLE 4

Results of chromatography of sample alditol acetate

| Peak | material | Retention time (min) | Standard concentration (mg/ml) | Relative retention time | Area (g) |
| --- | --- | --- | --- | --- | --- |
| 1' | uknown* | 15.03 | unknown* | 0.8290 | 0.1972 |
| 2' | Inositol | 18.13 | 10.004 | 1.0000 | 0.0344 |

*Substance originating from the inventive acidic polysaccharide

TABLE 5

| | | Mass spectral analysis of methylated alditol acetate | | | | | | | | | | | | | | | |
|---|---|---|---|---|---|---|---|---|---|---|---|---|---|---|---|---|---|
| Peak | Methylated | 43 | 45 | 71 | 87 | 99 | 101 | 113 | 115 | 117 | 129 | 139 | 145 | 161 | 189 | 205 | 233 |
| A | 2,3,4,6-Me$_4$-G | + | + | + | + |   | + |   |   | + | + |   | + | + |   | + |   |
| B | 2,3,6-Me$_3$-G | + | + |   | + | + | + | + |   | + |   |   |   |   |   |   | + |
| C | 2,4-Me$_2$-G | + |   |   | + |   | + |   |   | + | + |   |   |   | + |   |   |

3) Structural analysis of polysaccharide

Based on the combination of methylation by the Hakomori method with GC-MS, the determination of bond position was performed. In addition, through the nuclear magnetic resonance (NMR) analysis, the anomer analysis was performed to determine the bonding mode. Moreover, for identifying the methylation of polysaccharide, infrared absorption spectra were used.

Figure 3:
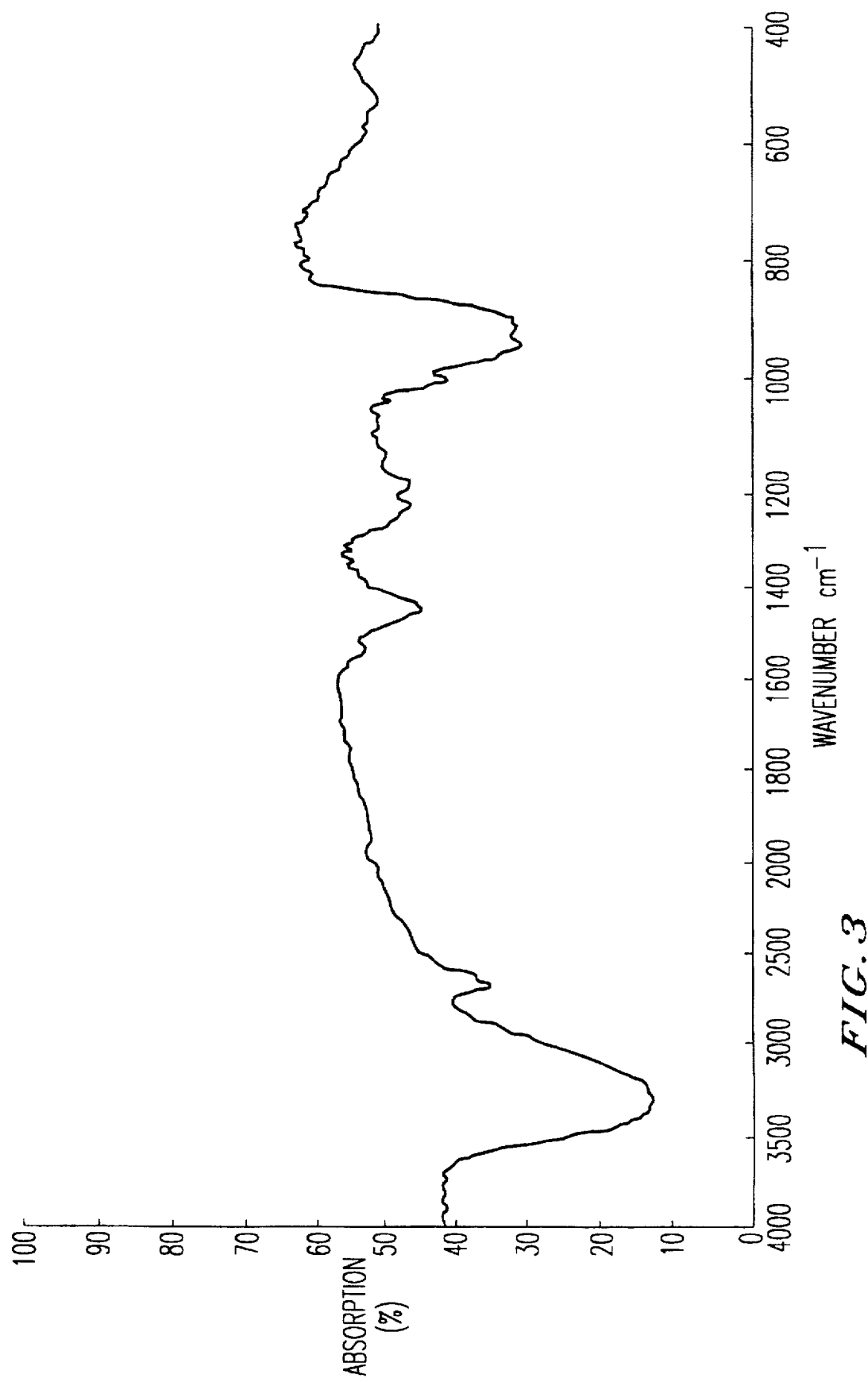
FIG. 3 shows an infrared absorption spectrum of the inventive untreated polysaccharide.
Figure 4:
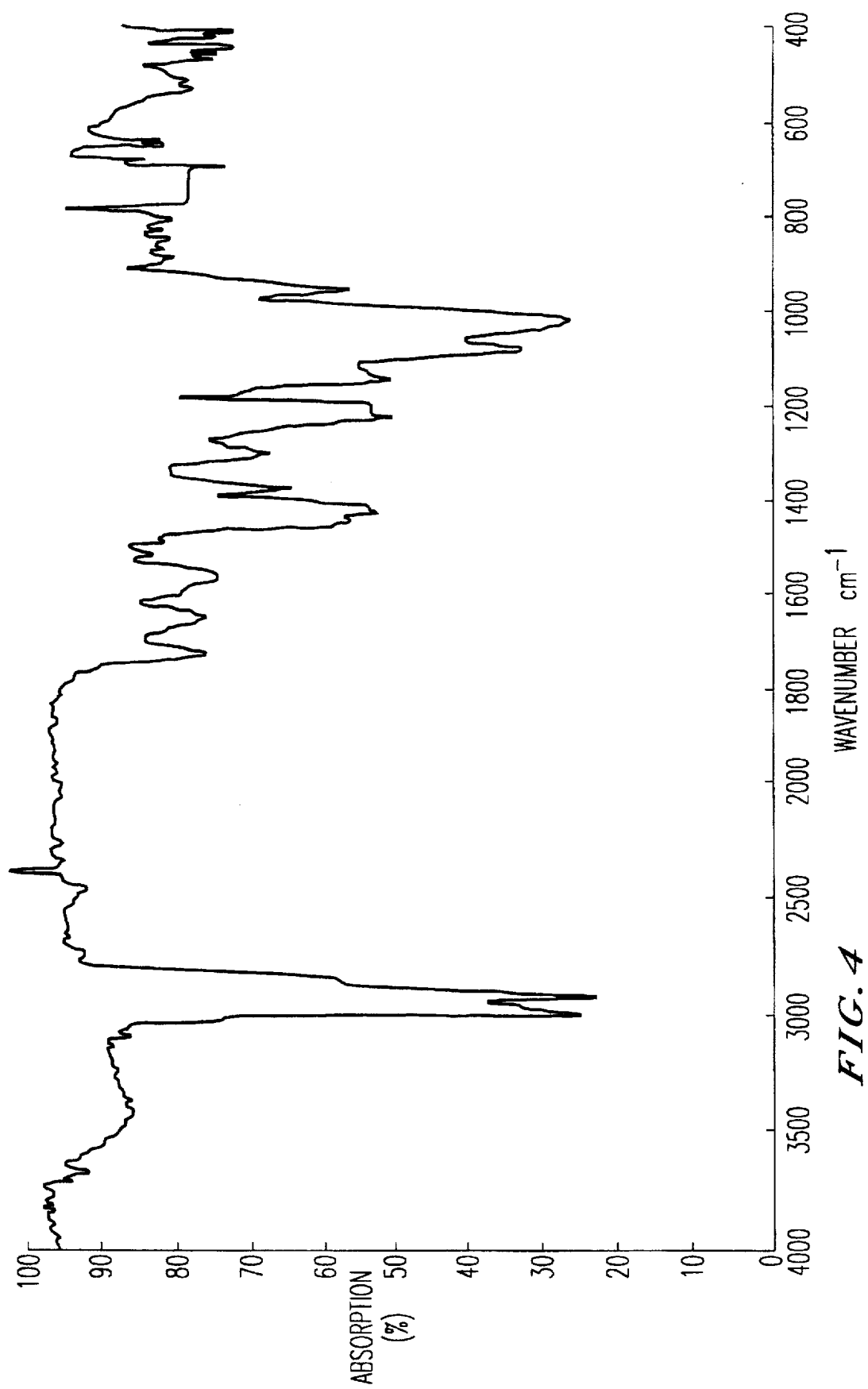
FIG. 4 shows an infrared absorption spectrum of the inventive methylated polysaccharide.
Figure 5:
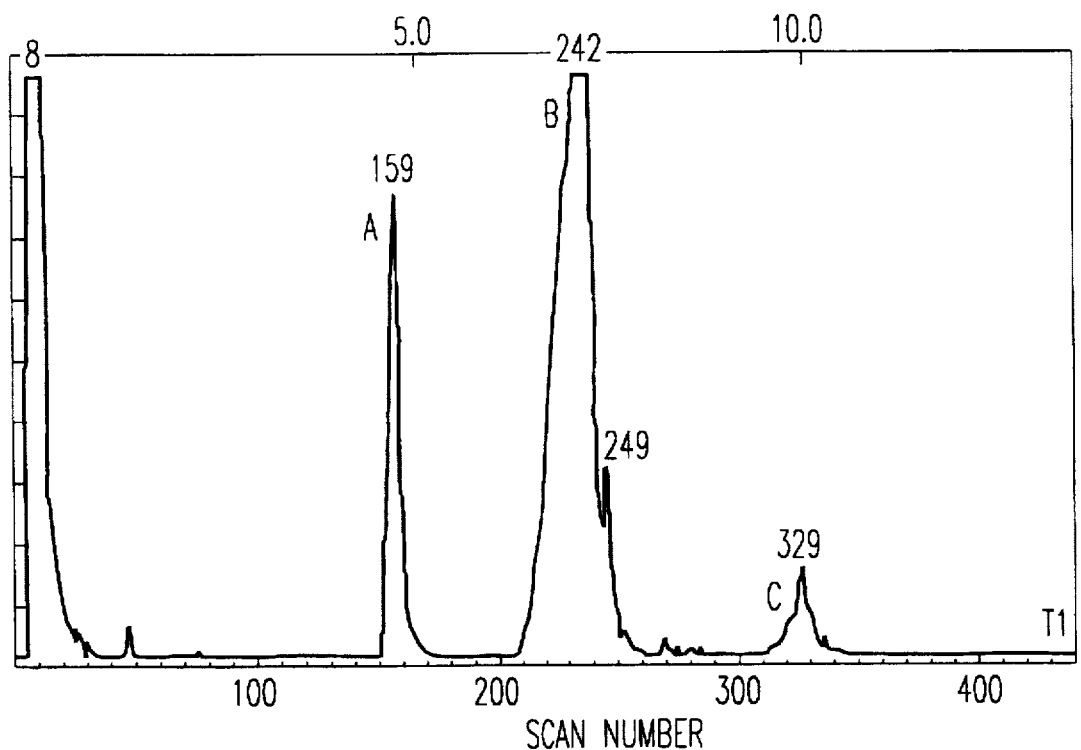
FIG. 5 shows an overall ion monitor of methylated alditol acetate of the inventive polysaccharide.
Figure 6:
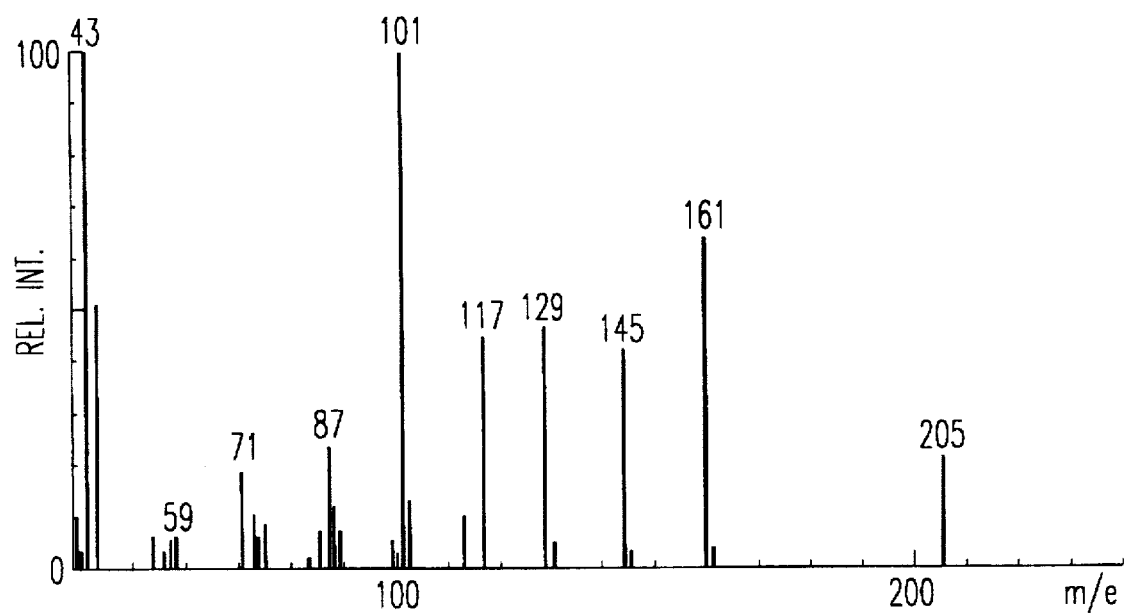
FIG. 6 shows a mass fragment-gram of methylated alditol acetate at Peak A of the inventive polysaccharide.
Figure 7:
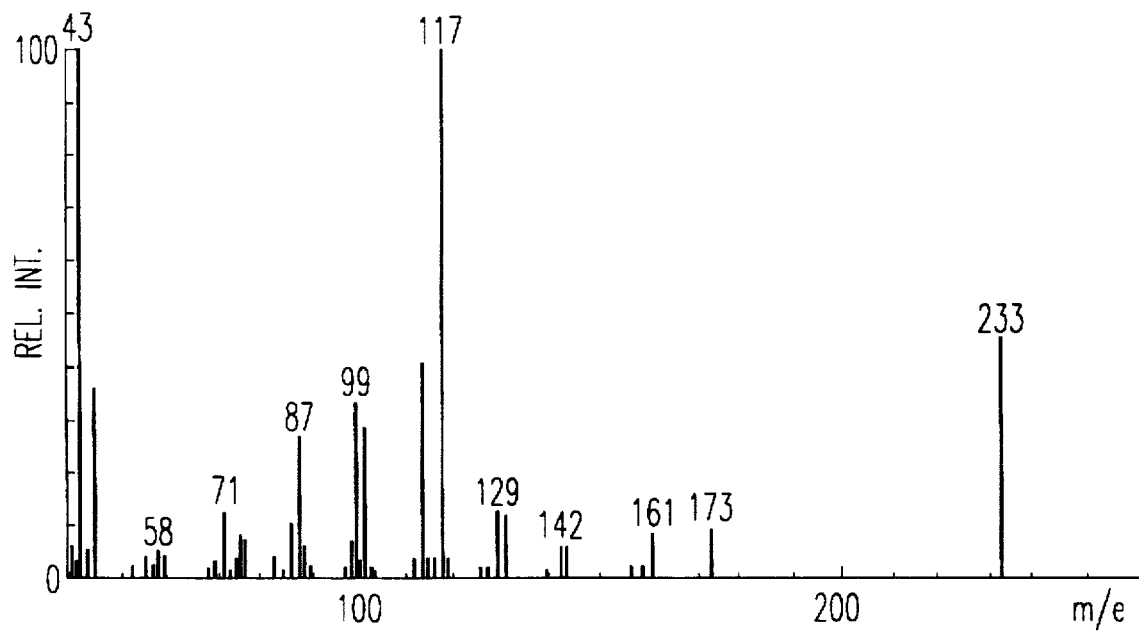
FIG. 7 shows a mass fragment-gram of methylated alditol acetate at Peak B of the inventive polysaccharide.
Figure 8:
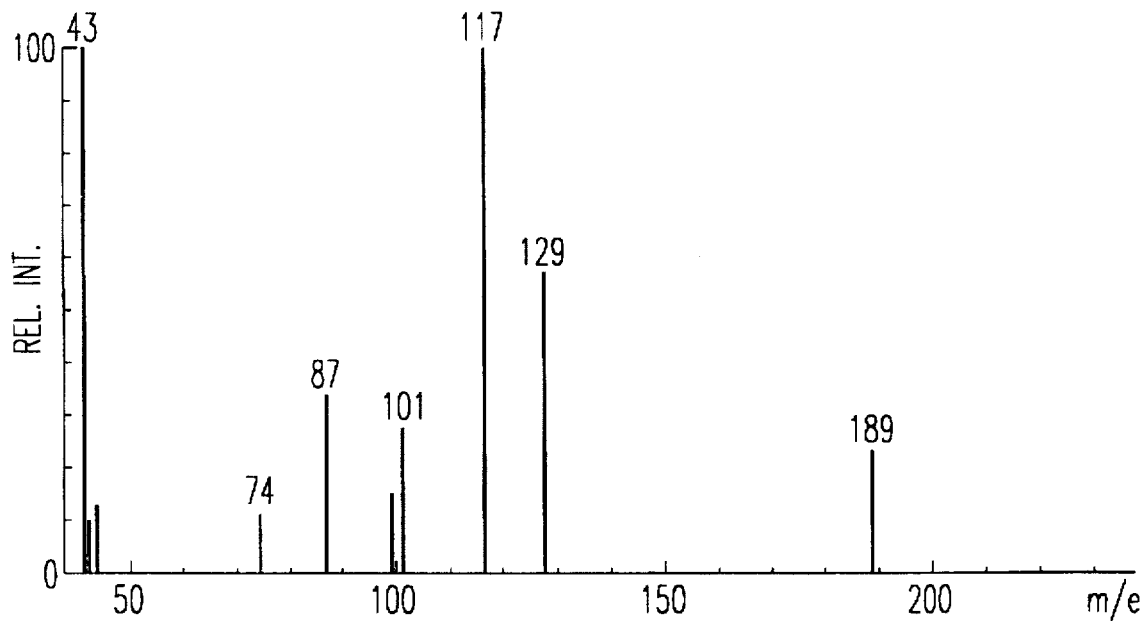
FIG. 8 shows a mass fragment-gram of methylated alditol acetate at Peak C of the inventive polysaccharide.

Comparing FIG. 3 showing an IR spectrum by KBr method using a dry polysaccharide sample with FIG. 4 showing an IR spectrum of methylated polysaccharide by KRS cell method, a strong absorption region is found near 3400 cm$^{-1}$ in the spectrum of FIG. 3, but it cannot be recognized in FIG. 4; instead, a strong absorption region is found at 2890 cm$^{-1}$, which indicates disappearing of hydroxyl group in polysaccharide due to methylation and appearing of methyl group.

The absorption region showing the feature of sugars lies at 730 to 960 cm$^{-1}$ in FIG. 4. Also, an absorption appearing to show Type 2 was recognized at 840 cm$^{-1}$ in FIG. 3 and at 858 cm$^{-1}$ in FIG. 4. An absorption appearing to show Type 3 was found at 760 cm$^{-1}$ in FIG. 3, but not identified in FIG. 4.

From the fact as described above, the orientation of the polysaccharide is α-type. Moreover, in FIG. 3, an absorption at 2950 cm$^{-1}$ that shows OH stretching, an absorption at 1730 cm$^{-1}$ that shows CO stretching and absorptions at 1650 cm$^{-1}$ and 1420 cm$^{-1}$ that appear to show the existence of carboxylate were recognized. Furthermore, the methylation of polysaccharide brings about the disappearance of absorptions at 2950 cm$^{-1}$ and 1650 cm$^{-1}$ and a drastic increase in absorption at 1730 cm$^{-1}$, as shown in FIG. 4. Based on this, carboxylic acid or uronic acid is present in the polysaccharide interposed as an ester group.

Next, from the analysis of mass spectra, Peak A was 2,3,4,6-Me$_4$-G as shown in Table 5. This can be seen to be nonreducing end group, since it is glucose having a bond only at C1. Moreover, Peak B was 2,3,6-Me$_3$-G. This shows 1,4 bond. Peak 3 was 2,4-Me$_2$-G, which shows 1,3,6 bond. Moreover, the percentages of peak area ratio were 13.4% for Peak A, 75% for Peak B and 11.62% for Peak C, respectively. Based on this fact, that the polysaccharide is a multibranched polysaccharide mainly composed of 1,4 bond with branches from 3- and 6-positions.

Figure 9:
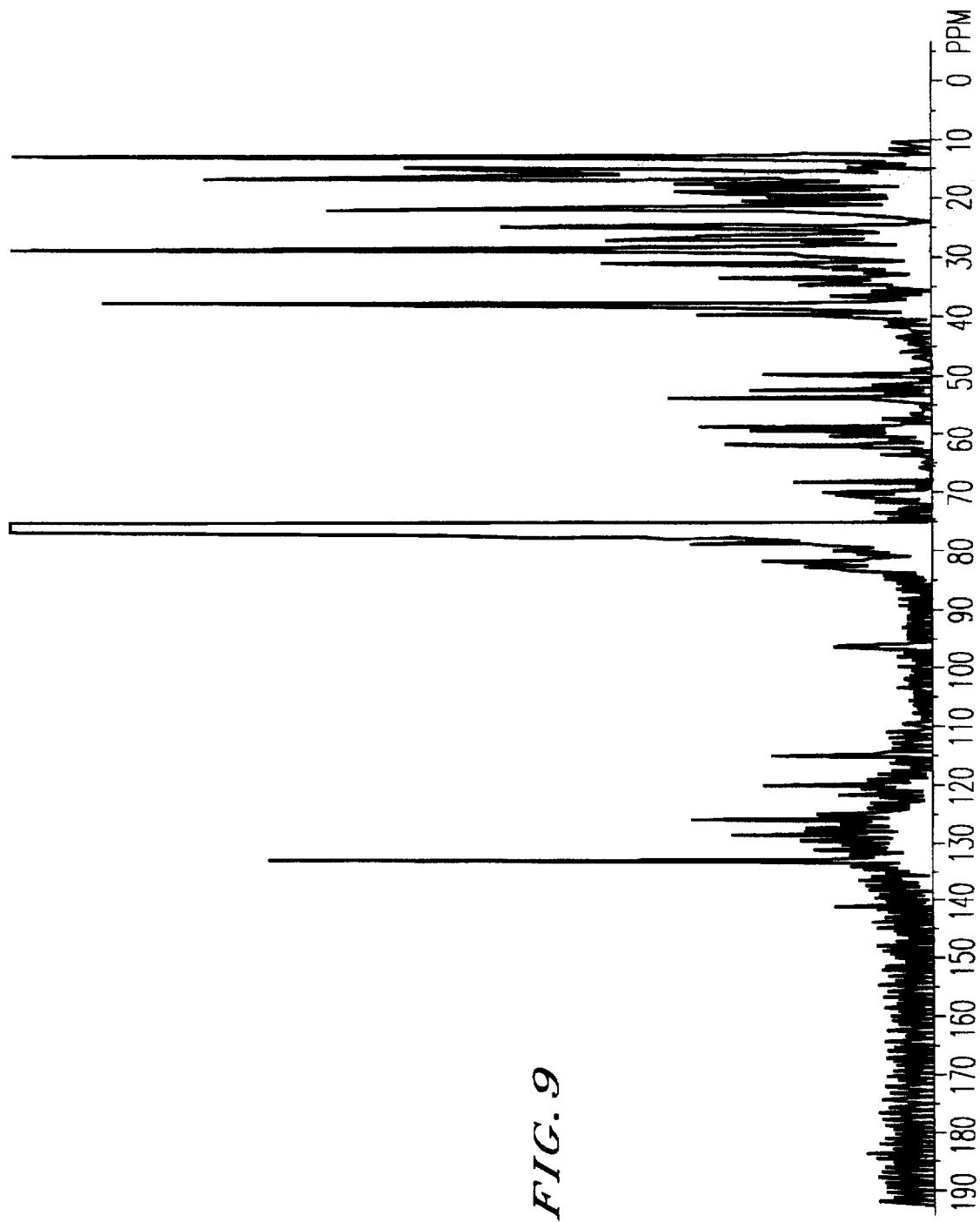
FIG. 9 shows a $^{13}C$ NMR spectrum of the inventive methylated polysaccharide.

Further, through the analysis of IR and MMR (shown in FIGS. 5, 6, 7 and 8), it was identified that, from C1 peak at 96.5 cm, the bonding mode was α-type and the orientation of anomer carbon of the polysaccharide was α, as shown in FIG. 9.

From above, the polysaccharide is a homoglucan, which is of α-type and in which the main chain has 1,4 bond with branches at 3- and 6-positions.

4) Qualitative analysis of organic acids

Since it was inferred from infrared absorption spectra that organic acids were contained in the polysaccharide interposing ester bond, the organic acids were identified by means of paper chromatography.

Namely, the purified polysaccharide solution was adjusted to pH 10.0 with 3% NaOH, which was shaked for 1 hour at 80° C. in a water bath. After cooling, a precipitate was induced with 70% ethanol, which was centrifugally separated for 15 minutes at 10000 rpm to obtain a supernatant. To this, cation-exchange resin Amberlite IR-120B was added, which was allowed to stand for over 3 hours to demineralize. This was filtered under suction through glass fiber filter GD-120, and the filtrate was dried at 40° C. under reduced pressure in an evaporator. This was converted to aqueous solution and submitted to paper chromatography. As a developer, supernatant of a mixed solution (1:1) of butanol solution containing 0.85M formic acid was used, and succinic acid, malic acid, tartaric acid and citric acid were spotted as standard substances. After development and drying, 0.05% alcoholic solution of BPB was sprayed as a coloring agent to generate color, thus detecting malic acid, citric acid and other unknown acids. From this analysis, we made the polysaccharide is an acidic polysaccharide.

Toxicity test

1) Acute toxicity test using mice

The intraperitoneal administration and the subcutaneous injection of the polysaccharide to a group of 5 mice showed no abnormality.

2) Subacute test through oral administration to mice

When the polysaccharide was administered forcedly by stomach sonde in amount of 0.1 ml per body weight to a group of 5 mice, no abnormality was recognized.

Breeding test of carp with present polysaccharide-added feed

1) Preparation of polysaccharide-added feed

Commercial carp-raising feed and the polysaccharide were formulated in proportions of 1:1 and 1:2 by weight, and the mixture was dried and pulverized in a mixer.

2) Feeding method of polysaccharide-added feed to carp

The carp were bred for 10 weeks from 12 weeks in age to 22 weeks in age. The carp were divided randomly in a 57-liter volume water tank such that one compartment of the tank with polysaccharide-added feed and one compartment of the tank with polysaccharide-free feed accommodated 20 carp, to the 20 carp in the compartment with polysaccharide-added feed, the polysaccharide-added feed was fed so that the intake of polysaccharide per day per carp amounted 0.2% of average body weight. Namely, 0.01 g was fed to 10 g of body weight. Accordingly, average body weight (g)× 0.001×20 was made to be an amount per day, and the feeding method was such that, at the time of feeding in the morning, polysaccharide-added feed was fed, and, at the time of feeding in the evening, polysaccharide-free feed was fed as much as eatable. The feeding of polysaccharide-free feed was also performed by a similar method. The feeding level during a period was measured by simultaneously weighing the body weights of 20 carp once a week with a balance, and the average from that result was made as a feeding level of polysaccharide-added feed for the next week.

3) Effect of polysaccharide-added feed on increase in body weight

Figure 10:
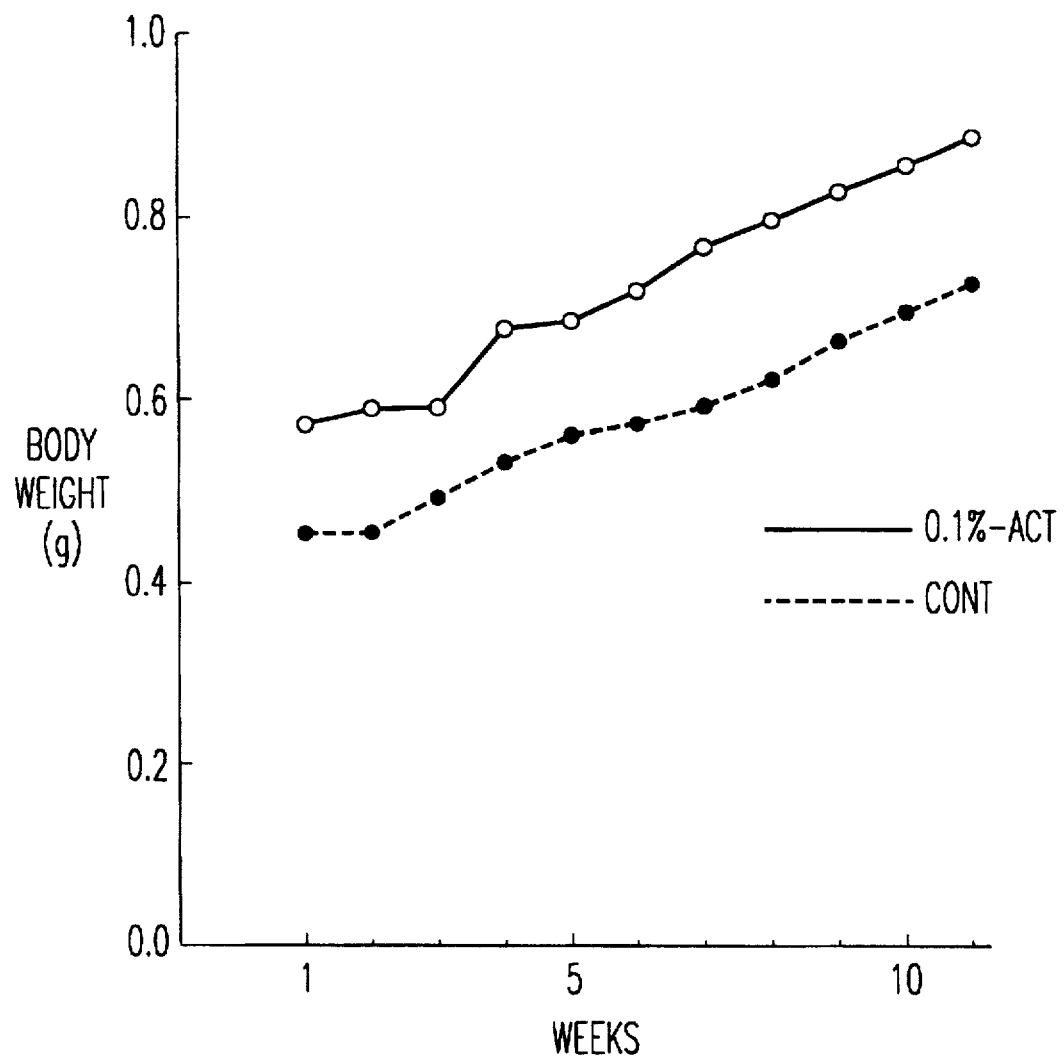
FIG. 10 is a chart showing an increase in average body weight of fish bred with a feed containing 0.1%, of the inventive polysaccharide.

The promotion effect of compartment with the polysaccharide-added feed and compartment with polysaccharide-free feed on body weight from 12 weeks in age to 22 weeks in age was 0.9 g for 22 week in age in the compartment with polysaccharide-added feed, while it was 0.7 g in the compartment with polysaccharide-free feed, as shown in FIG. 10, which shows the inventive polysaccharide increases body weight by an additional 0.2 g.

The acidic polysaccharide of the invention obtainable by culturing the acidic polysaccharide-producing germ belonging to *Aureobasidium sp.* has an agglutination activity and no toxicity, and it was recognized that it was effective for the promotion of growth by adding to feed and that it was also useful as a waste water-treating agent and a food additive.

What is claimed is:

1. A process for producing high-viscous acidic polysaccharide comprising the step of culturing an acidic polysaccharide-producing germ belonging to *Aureobasidium sp.* on a medium with lecithin and vitamin E added.

2. An acidic polysaccharide which is a homoglucan comprised of glucose residues, wherein the glucose residues in the main chain are bonded by α-1,4 linkages;

at least a portion of the 3- and 6-positions of the glucose residues in the main chain are branched; and at least a portion of the hydroxyl groups of the glucose residues are esterified with at least one carboxylic acid selected from the group consisting of malic acid and citric acid.

3. The acidic polysaccharide of claim 2, obtained by a process comprising isolating the acidic polysaccharide from an *Aureobasidium sp.* bacterium which produces the acidic polysaccharide.

4. The acidic polysaccharide of claim 2, obtained by a process comprising culturing an *Aureobasidium sp.* bacterium which produces the acidic polysaccharide, and isolating the acidic polysaccharide from the culture medium.

5. The acidic polysaccharide of claim 2, wherein a 0.1% solution of the purified polysaccharide has a relative viscosity of 2.721 as measured by an Oswald viscometer.

6. A process for producing the acidic polysaccharide of claim 2, comprising culturing an *Aureobasidium sp.* bacterium which produces the acidic polysaccharide, and isolating the acidic polysaccharide from the culture medium.

7. The process of claim 6, wherein the culture medium comprises lecithin and Vitamin E.

8. A food additive comprising the acidic polysaccharide of claim 2.

9. A composition comprising the acidic polysaccharide of claim 2 and at least one food.

10. The composition of claim 9, wherein the food comprises an animal feed.

11. A method of promoting the growth of an animal, comprising feeding a composition comprising the acidic polysaccharide of claim 2 to the animal.

12. The method of claim 11, wherein the composition further comprises an animal feed.

* * * * *